US007790118B2

(12) United States Patent
Maltezos et al.

(10) Patent No.: US 7,790,118 B2
(45) Date of Patent: Sep. 7, 2010

(54) MICROFLUIDIC DEVICES AND RELATED METHODS AND SYSTEMS

(75) Inventors: George Maltezos, Fort Salonga, NY (US); Axel Scherer, Laguna Beach, CA (US)

(73) Assignee: California Institute of Technology, Pasadena, CA (US)

( * ) Notice: Subject to any disclaimer, the term of this patent is extended or adjusted under 35 U.S.C. 154(b) by 337 days.

(21) Appl. No.: 11/874,213

(22) Filed: Oct. 18, 2007

(65) Prior Publication Data

US 2008/0145286 A1 Jun. 19, 2008

Related U.S. Application Data

(60) Provisional application No. 60/852,936, filed on Oct. 18, 2006, provisional application No. 60/905,788, filed on Mar. 8, 2007.

(51) Int. Cl.

| | |
|---|---|
| ***B01J 10/00*** | (2006.01) |
| ***C12M 3/00*** | (2006.01) |
| ***B01D 15/04*** | (2006.01) |
| ***F16K 7/00*** | (2006.01) |

(52) U.S. Cl. ........................ 422/129; 422/130; 422/224; 435/288.5; 435/289.1; 210/198.1; 210/638; 137/833; 137/863

(58) Field of Classification Search ................. 422/129, 422/130, 68.1, 224; 435/91.2, 288.5, 289.1; 536/122; 210/198.1, 638; 137/833, 863
See application file for complete search history.

(56) References Cited

U.S. PATENT DOCUMENTS

| | | | | |
|---|---|---|---|---|
| 6,168,948 | B1 * | 1/2001 | Anderson et al. | 435/287.2 |
| 6,406,605 | B1 * | 6/2002 | Moles | 204/601 |
| 6,408,878 | B2 | 6/2002 | Unger et al. | |
| 6,793,753 | B2 | 9/2004 | Unger et al. | |
| 6,889,137 | B1 | 5/2005 | Rychlak | |
| 6,929,030 | B2 | 8/2005 | Unger et al. | |
| 6,949,377 | B2 * | 9/2005 | Ho | 435/287.1 |
| 7,040,338 | B2 | 5/2006 | Unger et al. | |
| 7,122,153 | B2 * | 10/2006 | Ho | 422/58 |
| 7,144,616 | B1 | 12/2006 | Unger et al. | |
| 7,169,314 | B2 | 1/2007 | Unger et al. | |
| 7,216,671 | B2 | 5/2007 | Unger et al. | |
| 7,435,381 | B2 * | 10/2008 | Pugia et al. | 422/58 |
| 7,445,926 | B2 * | 11/2008 | Mathies et al. | 435/288.5 |
| 2002/0123059 | A1 * | 9/2002 | Ho | 435/6 |
| 2003/0210607 | A1 * | 11/2003 | Gilbert et al. | 366/152.1 |
| 2004/0132218 | A1 * | 7/2004 | Ho | 436/524 |
| 2004/0209354 | A1 * | 10/2004 | Mathies et al. | 435/287.2 |
| 2005/0196779 | A1 * | 9/2005 | Ho et al. | 435/6 |
| 2005/0221281 | A1 * | 10/2005 | Ho | 435/4 |
| 2005/0274227 | A1 * | 12/2005 | Aggarwal et al. | 75/710 |
| 2006/0166357 | A1 * | 7/2006 | Takayama et al. | 435/289.1 |
| 2006/0263818 | A1 | 11/2006 | Scherer et al. | |
| 2007/0026439 | A1 * | 2/2007 | Faulstich et al. | 435/6 |
| 2008/0013092 | A1 | 1/2008 | Maltezos et al. | |
| 2008/0142157 | A1 | 6/2008 | Maltezos | |

* cited by examiner

*Primary Examiner*—Walter D Griffin
*Assistant Examiner*—Huy-Tram Nguyen
(74) *Attorney, Agent, or Firm*—Steinfl & Bruno

(57) ABSTRACT

In a fluidic device with a storage compartment communication is allowed between the storage compartment and other portions of the device. The communication is controlled through a valve arrangement and a membrane covering the compartment. The valve arrangement can be provided through a sealing clamp with clamp fingers. The clamp fingers control communication between the storage compartment and remaining portions of the fluidic device.

26 Claims, 12 Drawing Sheets

MICROFLUIDIC DEVICES AND RELATED METHODS AND SYSTEMS

CROSS REFERENCE TO RELATED APPLICATIONS

This application claims priority to U.S. Provisional Application Ser. No. 60/852,936 filed on Oct. 18, 2006, entitled “Dot Matrix Style Pin Operated microfluidic Valve” and Ser. No. 60/905,788 filed on Mar. 8, 2007 entitled “Microfluidic Biological Testing Device with Integrated Reagent Storage”, the content of both of which is incorporated herein by reference in their entirety.

STATEMENT OF GOVERNMENT GRANT

This invention has been made with U.S. Government support under Grant No. HG0026440 awarded by the National Institutes of Health. The U.S. Government has certain rights in this invention.

TECHNICAL FIELD

The present disclosure relates to the field of microfluidics and in particular to microfluidic devices and related methods and systems.

BACKGROUND

Microfluidic devices and systems are commonly used in the art for processing and/or analyzing of very small samples of fluids. In such microfluidic devices and systems, the integration of many elements in a single microfluidic device has enabled powerful and flexible analysis systems with applications ranging from cell sorting to protein synthesis. Some microfluidic operations that are functional to the performance of said applications include mixing, filtering, metering pumping reacting sensing heating and cooling of fluids in the microfluidic device.

Many different approaches have so far been explored for performing said operations in a microfluidic environment, including combining thousands of lithographically defined components, such as pumps and valves, into chip based systems to achieve control over reagents concentrations and reactions' performance.

SUMMARY

According to a first aspect, a microfluidic device is disclosed, the microfluidic device comprising a storage compartment, a reaction area, a microfluidic channel, a valve arrangement and a membrane. In the microfluidic device, the storage compartment is adapted to comprise a reagent suitable for a reaction to occur in the microfluidic device, and the reaction area, is an area where a reaction involving said reagent is adapted to occur. In the microfluidic device, the microfluidic channel connects the storage compartment with the reaction area and the valve arrangement, to control opening and closing of the microfluidic channel. In the microfluidic channel, the membrane adapted to cover at least portion of the storage compartment, reaction area, and microfluidic channel, the membrane being also adapted to seal the at least portion of storage compartment, reaction area, and microfluidic channels, in particular upon filling of the storage compartment with the reagent.

According to a second aspect, a hermetically sealed bag is disclosed, the sealing bag comprising the microfluidic device described above.

According to a third aspect, a machine reader is disclosed, the machine reader comprising the microfluidic device described above.

The details of one or more embodiments of the invention are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description, serve to explain the principles and implementations of the complexes, systems and methods herein disclosed.

In the drawings.

Like reference symbols in the various drawings indicate like elements.

DETAILED DESCRIPTION

Figure 1:
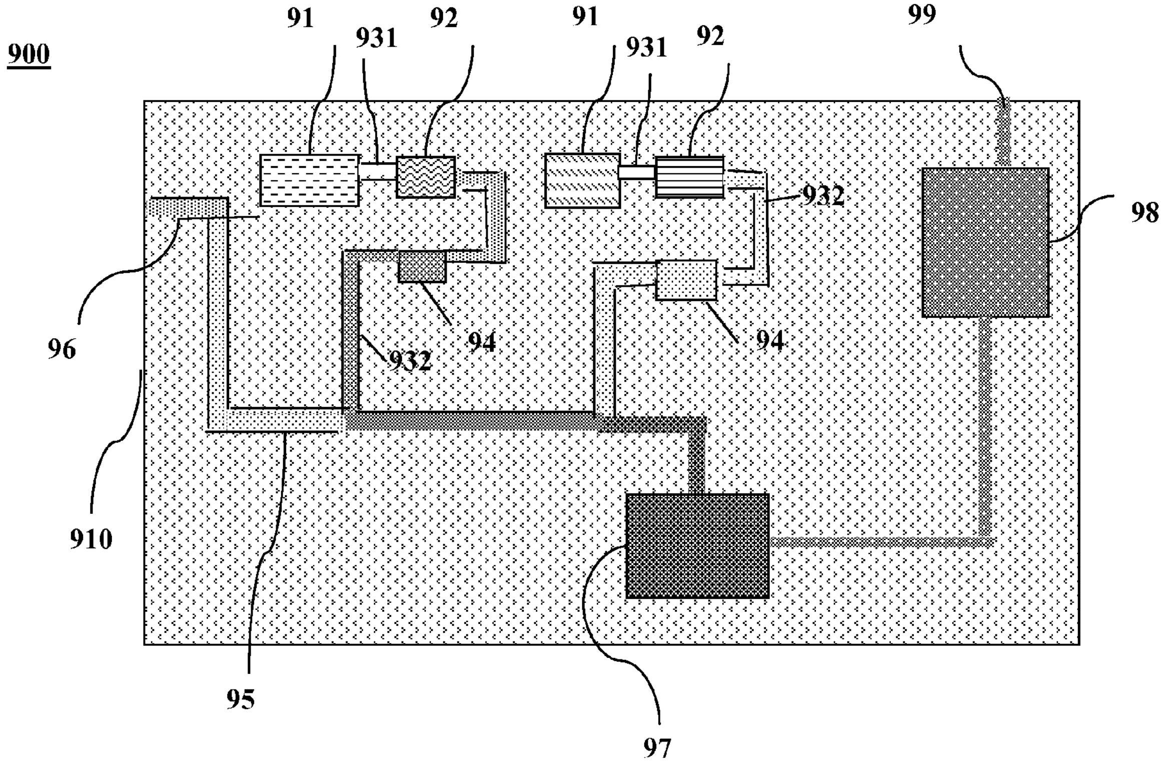
FIG. 1 shows a top sectional schematic view of a microfluidic chip according to an embodiment herein disclosed.

A microfluidic device is herein disclosed that is adapted to include a storage compartment comprising a reagent suitable for a reaction to be performed in the microfluidic device.

In particular, in some embodiments, a sample preparation chip is disclosed that can be stored, e.g. at room temperature, for a predetermined period of time, and especially for long periods of time, while storing all necessary reagents to operate the chip in a determined state. The storage state of the reagent is compatible with a desired temperature of storage (e.g. lyophilized for room temperature storage). In some embodiments, the temperature of storage is from 4° C. to room temperature.

When use of the chip is desired, the reagent might need to be brought to a state where they can be used in a reaction mixture. For example, in embodiments wherein a reagent is lyophilized, the reagent can be contacted with a liquid, such as water, to be reconstituted. In some of those embodiments, the reagents in lyophilized form and the liquid can be stored in separate compartments of the same chip or device. In particular, in some embodiments, at least two storage compartments are provided in the chip and connected to each other by way of a valve regulated channel. When storage of the substances stored is desired, the valve is closed and no communication occurs between the two compartments. When use of the chip is desired, the valve is opened, thus putting the two storage compartments in communication thus allowing reconstitution of the reagent(s) stored therein.

In some embodiments, the storage compartment is covered by a deformable membrane, such as a SIFEL membrane, that can be operated in combination with a valve arrangement reversibly closing the channel connecting the storage compartments by pinching the deformable membrane. In those embodiments, the use of a material to cover the compartment that is different from the material of the compartment, allows to obtain chemically robust storage compartments able to hold all sort of solvents, including ethanol, and to be operated with a valve system that allows the solvents to be released in other compartments of the chip, when desired.

In some embodiments, the membrane made of deformable material covers also additional non-storage compartments and/or microchannels, and the valve arrangement used to release the reagents from the storage compartments can advantageously be one of the valve arrangements previously described.

In some embodiments, the chip including the storage compartment herein described can be manufactured by 1) providing a base layer, 2) providing cavities in the base layer that will form channel(s) and compartment(s) of the microfluidic chip; 3) filling at least one of the cavities with a substance of interest; and 4) providing a membrane of deformable material to cover the cavities. In particular, the deformable membrane can be contacted with the base layer to seal the cavities. In some embodiment, the microfluidic device includes one storage compartment connected to a reaction area by a channel. In some embodiments the microfluidic device includes two or more storage compartments connected to a reaction area and to each other by a channel.

In the exemplary illustration of FIG. 1, a chip or device (900) is shown that includes a base layer or matrix (910) with a liquid storage compartment (91) and a dry storage compartment (92) connected to each other by a channel (931) and to a reaction area (97) through channels (932) and (95). Opening and closure of the channels can be controlled, for example, through dot matrix style pin operated valves such as the ones later described in greater details (see FIGS. 9 through 15.)

The reaction area (97) is connected to a sample port including a filter (96) e.g. a Pall® or Whatman® blood filters) and to a waste area (98). The waste area (98) is connected to a vent (99). In operation, vacuum can be applied to the vent (99), possibly through a vapor barrier filter embedded in the channel, or otherwise attached or sealed to the chip and the vacuum in combination with the dot matrix style pin operated valves (not shown) controls the flow of fluids in channels (932) and (95) from the compartments (91) and (92). Mixers (94) can be located along the channels (932) to mix the substance of interest released from the liquid storage compartment (91) and the dry storage compartment (92), thus improving homogeneity of the reagents constituted. Several types of mixers can be used that are identifiable by a skilled person and will not be described herein in further detail.

In the embodiment of FIG. 1, the clamp can also have a port blood capillary input thread in it, to allow blood to be sampled through filter (96). See, for example, U.S. Ser. No. 11/804,112 filed on May 17, 2007 and directed to a fluorescence detector, filter device and related methods, which is incorporated herein by reference in its entirety.

Figure 2:
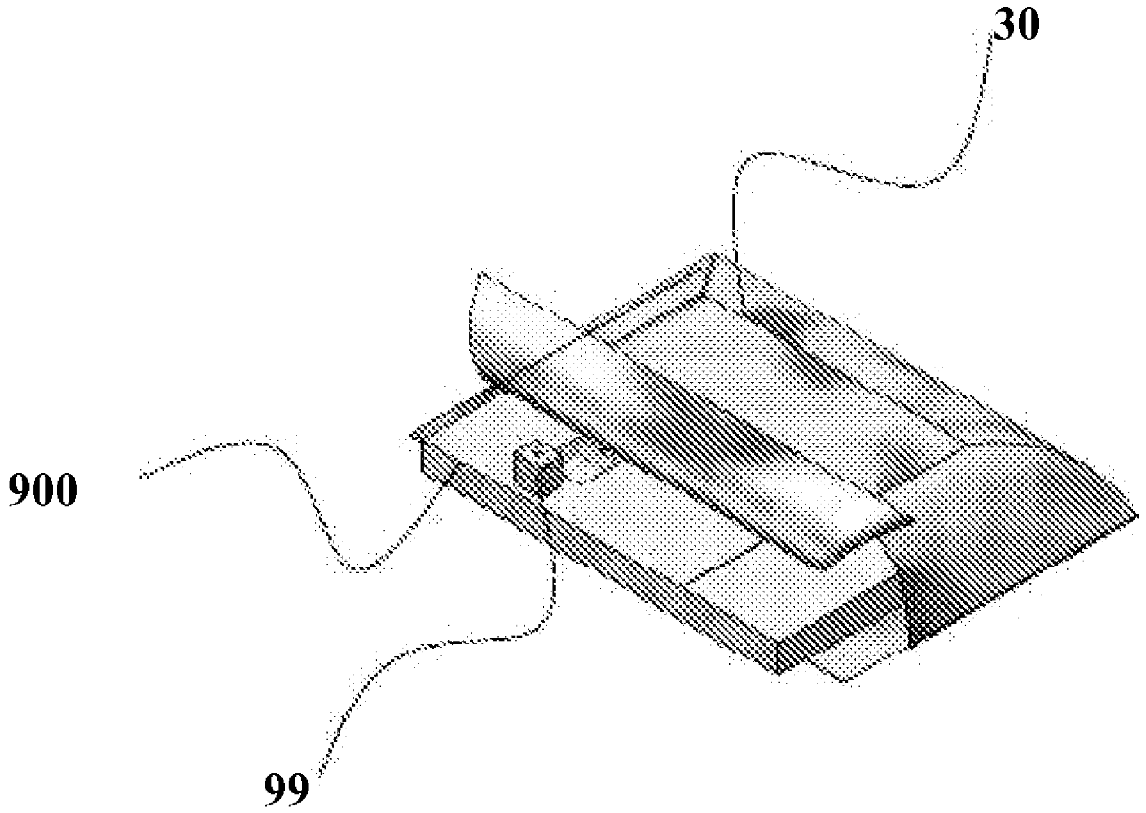
FIG. 2 shows a schematic prospective view of a microfluidic chip herein disclosed in an hermetic packaging according to another embodiment herein disclosed.

In some embodiments, illustrated in FIG. 2, the chip or device (900) is meant to be stored in a hermetically sealed and light-tight bag (30), which can be made of an opaque material, to be opened only when the chip, device or card is to be used.

Figure 3:
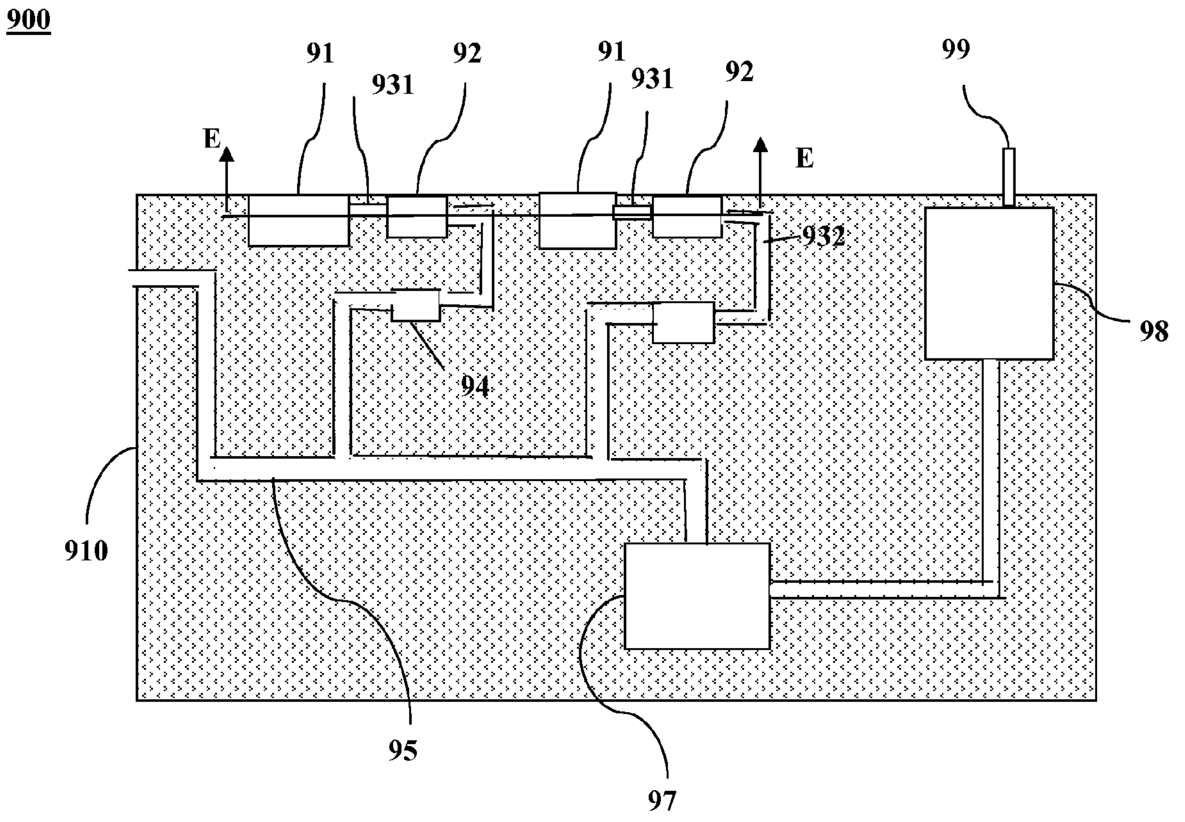
FIG. 3 shows a top sectional schematic view of a microfluidic chip according to a further embodiment herein disclosed.

In some embodiments, illustrated in FIG. 3, the chip (900) is manufactured to allow placement of a substance in compartments (91) and (92) before closure of the compartment with a cover element, that in preferred embodiments is formed of a deformable thin membrane.

In those embodiments, the bottom of the chip or card (900) can be an injection molded plastic card with the channels defined in it. The top section of the card can be a polymer which is molded in a thin layer and adheres to the plastic without blocking the channels as discussed previously in more detail. Suitable polymers include but are not limited to several versions of SIFEL and any other polymer that is impermeable to liquid and gas (preserving the reagents inside) and possibly flexible enough to act as a valve membrane if actuated by a pin or plunger as previously described (see, e.g., FIGS. 1 to 3 of the present application).

In the embodiments exemplified by FIG. 3 a cover is formed with a spun layer of deformable material, such as SIFEL with Teflon spacers disposed along the portion of the chip including the storage compartments (91) and (92) as well as microchannels (931) to prevent bonding of SIFEL with the matrix (910). In some embodiments, the spacer can be included to form storage pockets in the matrix (910), so that when the storage pockets are removed, pockets such as compartments (91) and (92) are formed. These pockets/compartments (91) and (92) can then be filled from the top with any substance of interest and sealed with the thin membrane (912) held to the plastic substrate with the clamp (950), e.g. a plastic clamp.

Figure 4:
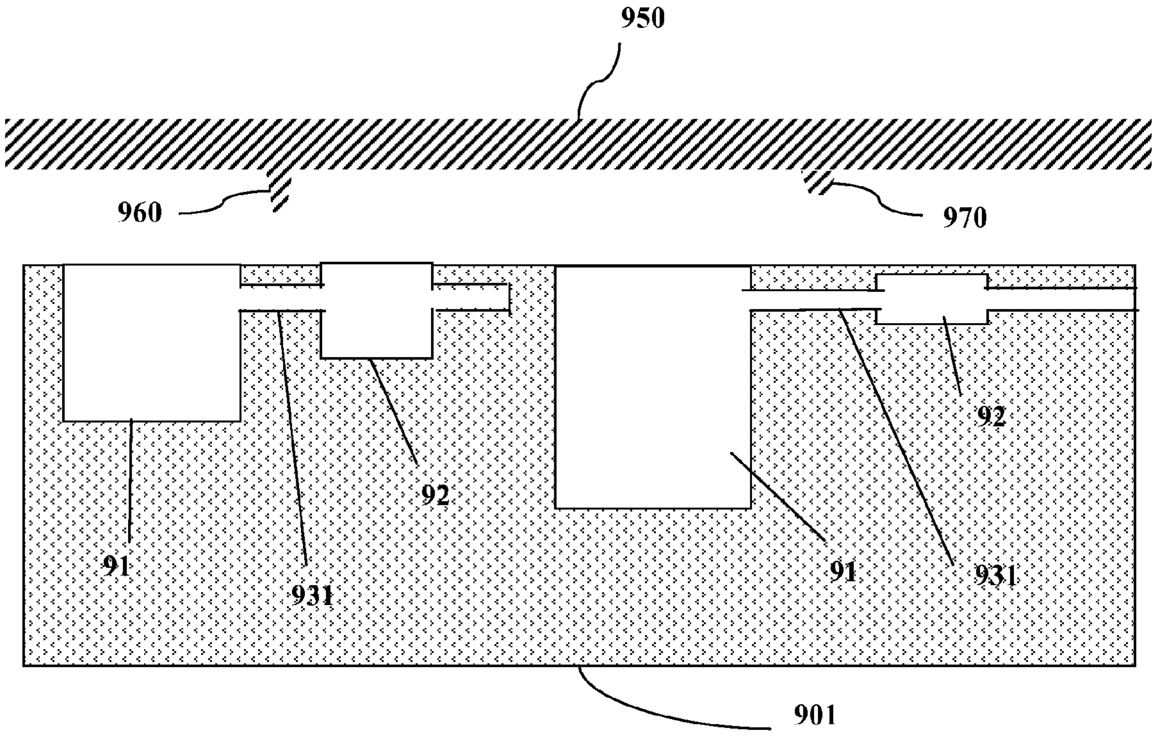
FIG. 4 shows a schematic enlarged cross sectional view of the microfluidic chip of FIG. 1 along line E-E of FIG. 3, also including a schematic cross-sectional illustration of a clamp according to an embodiment here disclosed.

In some embodiments, illustrated by the exploded sectional view of FIG. 4, the element clamp (950) includes clamp fingers (960) and (970), to be located along corresponding channels (931), to control opening of the channels (931) and consequently communications between compartments (91) and (92).

In operation, clamp fingers (960) and (970) are operated to allow communication between compartments (91) and (92). When desired, vacuum and the dot matrix pin operated valve can direct the flow of fluid from the compartments (91) and (92) to reaction chamber (97), see previously described FIG. 1.

The clamp (950) illustrated in the exploded sectional view of FIG. 4, will seal the liquid and dry storage wells shut, as well as provide a base for integrated valve clamps which are clamp fingers (960), (970) that stretch out from the clamp (950) and pinch off the channels (931) that extend from the storage chambers to the rest of the chip or card. The clamps clamp fingers (960), (970) can be electromechanically actuated without disturbing the main clamp (950) by bending of the valve clamps to open the chamber to communication with the microfluid circuit.

In some embodiments, the chip, device or card (900) is also meant to be used in a machine reader or controlling unit such as the controlling unit (2) illustrated in more detail later in this disclosure (see FIG. 15). The reader will provide vacuum for introducing the sample through the chip and will also electromechanically actuate the valves made with a polymer membrane as well as clamp fingers (960, 970) which separate the liquid from the lyophilized reagents.

In some embodiments, the thin membrane can be used as a pump by just pushing on it with mechanical means to push fluid. The thin membrane can also be actuated electromechanically as described herein. In some embodiments, a plurality of pump valves (e.g. 3 pump valves) can be actuated in connection with the thin membrane as a peristaltic pump.

In some embodiments, the vent (99) already shown with reference to previously described FIGS. 1 and 3 can have a filter, e.g., a vapor block of the sort used in vapor barrier pipette tips to prevent the reading machine from becoming contaminated.

In some embodiments, where the waste compartment (98) and/or the channels connecting the waste compartment (98) with the outside of the chip (900) are also covered with a layer of deformable material, the waste can also be stored on the card, and in particular locked in place by the clamp valves such as previously described clamp (950) at the time the card is removed, thus making it safe to dispose of the card.

The clamp (950) and associated valves or clamp fingers (960, 970) will be described in greater detail in the following illustrations of FIGS. 5 to 8.

Figure 5:
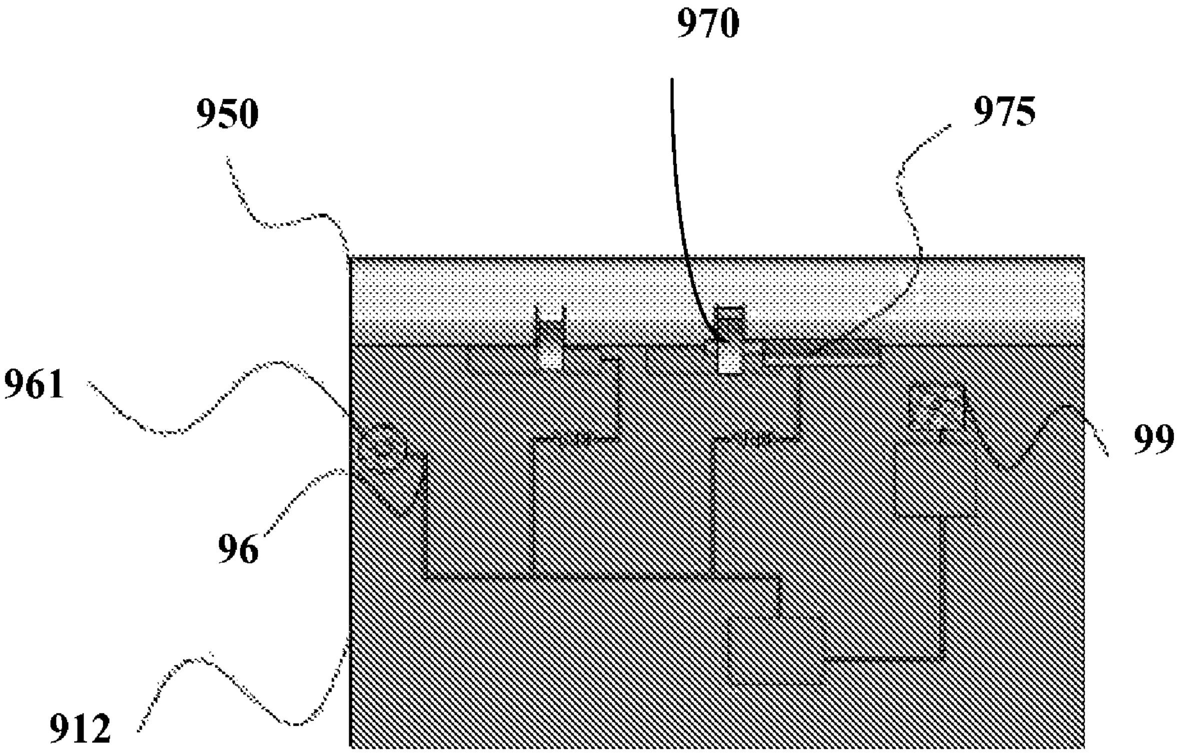
FIG. 5 shows a schematic top view of a microfluidic chip according to an embodiment herein disclosed.
Figure 6:
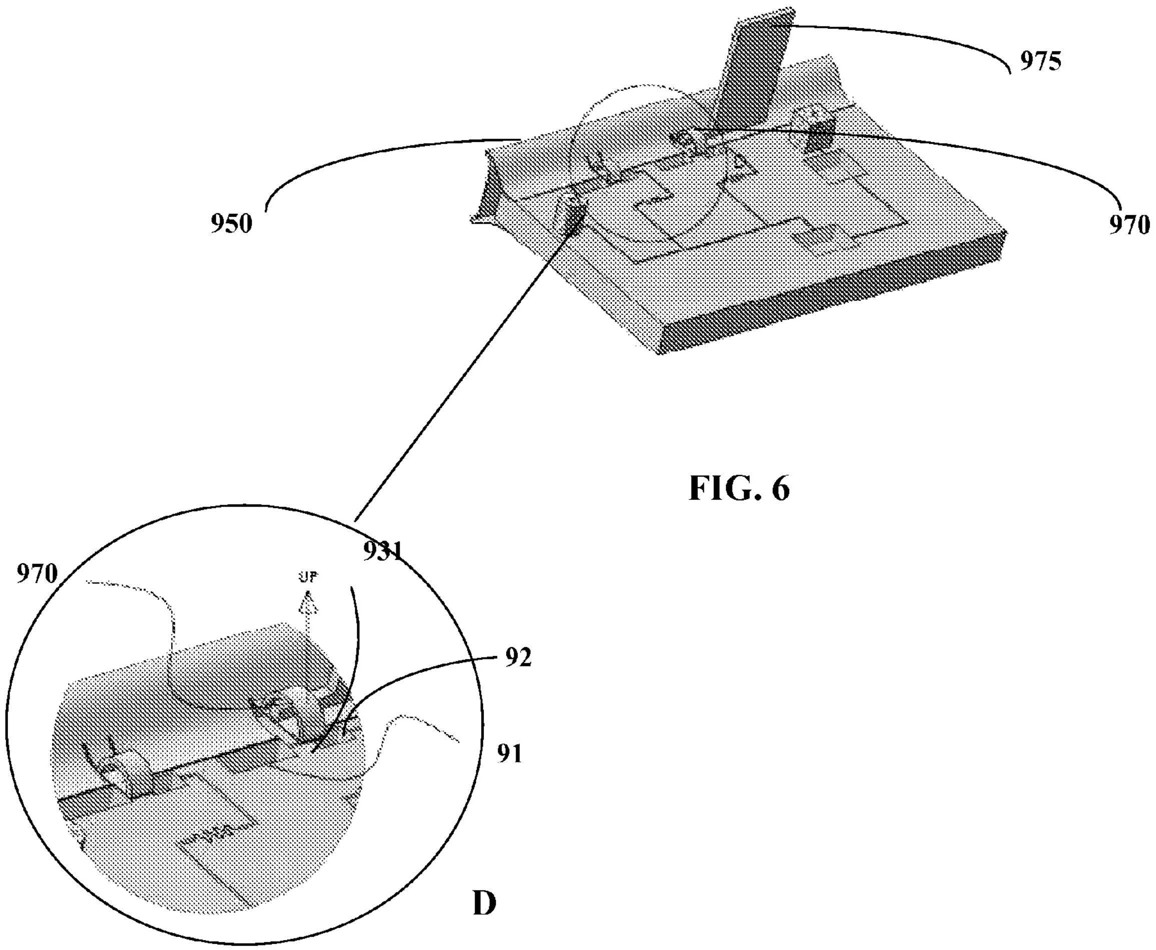
FIG. 6 shows a schematic top perspective view of a microfluidic chip according to an embodiment herein disclosed.

In the top view of FIG. 5 and perspective view of FIG. 6 the clamp (950) is shown together with a finger (970) and associated finger moving lever (975). Both clamp (950) and its finger (970) exert a spring-like force on the deformable membrane layer (912) formed on the chip, device, circuit or card (900) sealing it to the chip, thus forming a closed sealed storage/reaction vessel with all reagents. In particular, the spring force exerted by the finger (970) reversibly closes the channel (931) (see inset D of FIG. 6) between compartments (91) and (92). The spring force exerted by the clamp (950) contributes to hold in place the membrane (912) onto a matrix (910) of chip (900), as also illustrated in FIG. 7.

Figure 7:
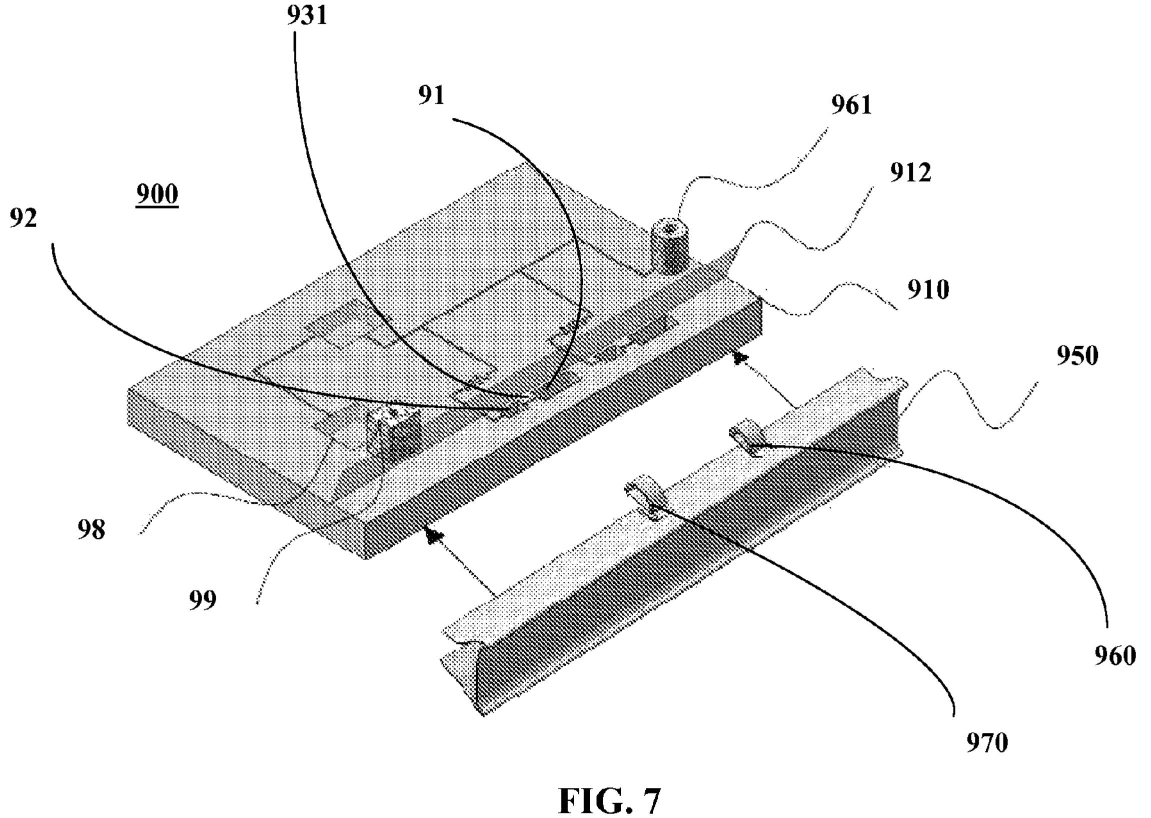
FIG. 7 shows a top perspective view of a microfluidic chip according to an embodiment herein disclosed.
Figure 8:
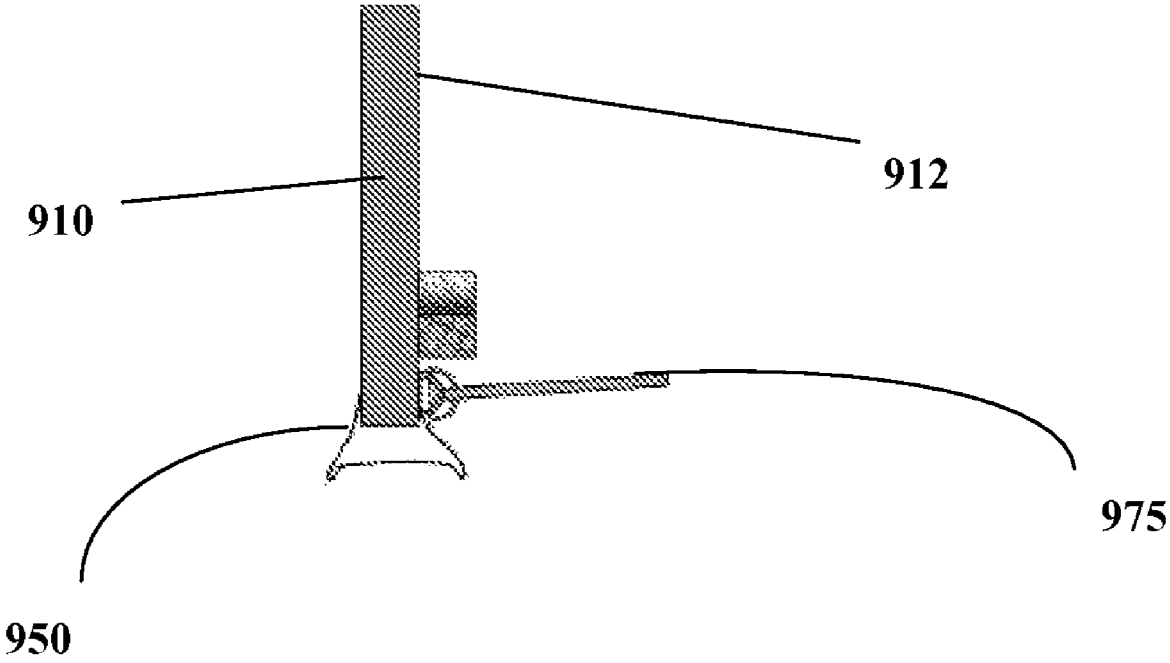
FIG. 8 shows a side view of a microfluidic chip according to an embodiment herein disclosed.

In the illustration of FIG. 7, the chip (900) including matrix (910) and thin membrane (912) is shown in a perspective view, with the thin membrane (912) lifted over the compartments (91) and (92) and the connecting channels (931). In this figure, clamp (950) is shown disengaged from the chip (900), and the thin membrane (912) lifted over the base layer (910). Upon engagement of clamp (950) with chip (900), the compartments (91) (92) and related channel (931) will be sealed. When storage is desired, the compartments (91) and (92) can be filled with the substance or substances of interest before sealing the compartments with the thin membrane (912) held in place by the clamp (950). As also explained before, the microchannel (931) can be closed by way of clamp fingers (960, 970). As it will be noticed by a skilled person, clamp (950) and clamp fingers (960, 970) can be operated independently so that it will be possible, for example, to selectively open/close some of the microchannels by operating one finger without altering the sealing effects associated with the clamp and/or other fingers. Although the clamps and fingers are often discussed in the present disclosure with reference to embodiments wherein the microfluidic device includes two or more storage compartments, the clamp and/or fingers can also be used in connection with a fluidic or microfluidic device including a single storage chamber as will be understood by a skilled person upon reading of the present disclosure.

In some embodiments the microfluidic device can be operated in a microfluidic assembly herein described, wherein a microfluidic valve arrangement is provided. The microfluidic valve arrangement allows control of the flow in one or more microfluidic channels of the microfluidic assembly.

Figure 9:
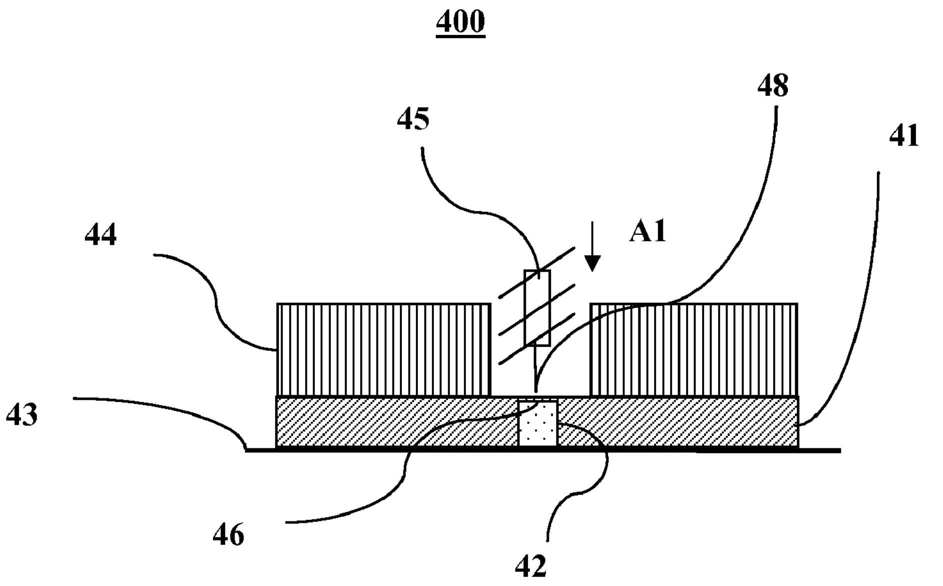
FIG. 9 shows a schematic cross sectional view of a valve arrangement according to an embodiment herein disclosed.
Figure 10:
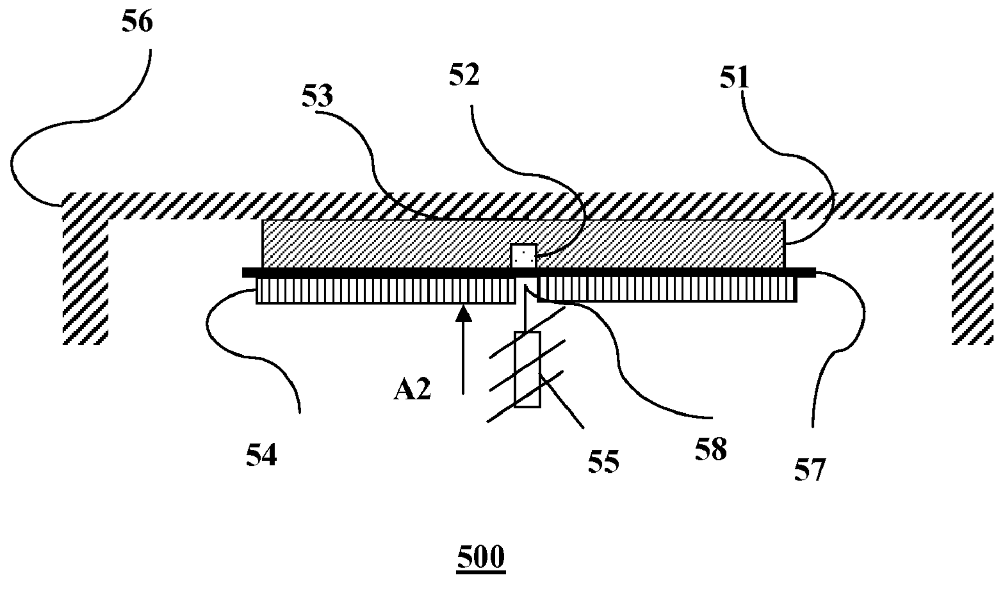
FIG. 10 shows a schematic cross sectional view of a valve arrangement according to another embodiment herein disclosed.

In particular, in some embodiments, the microfluidic valve arrangement is comprised of an electromagnetic solenoid actuator and of a thin membrane, wherein the solenoid actuator is used to actuate the microfluidic valve through direct compression of the thin membrane as illustrated further in the exemplary embodiments of FIGS. 9 and 10. Alternatively, the solenoid actuator can be combined with a hydraulic system in order to provide a valve arrangement acting as a microfluidic pump, as exemplarily illustrated in the embodiment of FIG. 11.

In the exemplary embodiment shown in FIG. 9, a microfluidic assembly (400) is illustrated, including a microfluidic chip or device (41) on a substrate (43). As shown in FIG. 1, the microfluidic chip comprises a microfluidic fluidic channel (42) and a thin membrane (46) along the upper side or top surface of the microfluidic channel (42).

In the microfluidic assembly (400) illustrated in FIG. 9, the valve arrangement is comprised of a solenoid actuator (45) and the thin membrane (46). In particular, the solenoid actuator (45) can be an actuator such as that used in a dot matrix printer type electromagnetic solenoid pin. As later described in the present application, the valve arrangement can be operated by a control unit connected to the solenoid actuator (see FIGS. 14 and 15).

In particular, each valve includes a tiny metal rod, wire or pin (48). Rod (48) is driven forward by the electromagnetic power of the solenoid, either directly or through small levers. Specifically, upon input from the control unit, current goes through the solenoid (45) and the pin (48) moves up and down by way of induced magnetic forces while the solenoid (45) stays in position In particular, when in operation, pin (48) is pushed down along the direction of the arrow A1 to deform portion (46) of the chip (41) and close channel (42), thus blocking flow passage inside the channel (42). The material of the membrane (46) and the shape and configuration of channel (42) are selected to be deformable and ensure closure of the channel (42).

In some embodiments, the microfluidic chip (41) can be a thin fluidic chip 10-100 micron tall. The channel (42) and substrate (43) can have variable dimensions. In particular, the dimensions and shape of channel (42) are functional to the desired valve effect and can vary in view of the material forming the channel and additional parameters such as thickness of the thin membrane (46) and material forming the thin membrane.

The thickness of the thin membrane (46) can be selected in view of the shape and dimensions of the channel (42) and the force exerted by the solenoid (45) on such membrane, so that the force of the solenoid is sufficient to depress the thin membrane (46) and deform it to the extent of closing the channel (42) without piercing the membrane or affecting the ability of the membrane (46) to seal the channel.

Preferably, the dimensions of the channel (42) and the thickness of the membrane (46) are controllable, to obtain a balance that allows to reversibly close the channel, by use of the spring constant of the deformable material of choice.

In addition to membrane thickness, channel shape and ability of the material forming the thin membrane to provide a spring effect, additional properties of the material forming the thin membrane, such as robustness, can be taken into account to ensure proper functioning of the membrane while preventing the solenoid from piercing the membrane, considering thickness and shape of pin (48). In some embodiments the shape of the channel is rounded an in particular the shape of the bottom of the channel is rounded so that at least portion of the surface match a corresponding rounded surface on the lower portion of the pin.

In some embodiments, the channel (42) is a microchannel with a width ranging from about 2 microns to about 1000 microns, usually about 200 microns selected to closely match the dimensions of the solenoid (45). The height of the channel can be (usually ranging from about 2 microns to about 300 microns) to allow proper fitting of the one into the other. As to the other dimensions of the channel, such as depth and height, dimensioning will depend on the ability of the solenoid (45) to depress the thin membrane (46) and can be from about a quarter of millimeter to about a millimeter.

The above dimensions correspond to standard measures that can be desirable when the use of standard component is desired. However, the valve arrangement of the present disclosure can also be manufactured with customized parts and dimensions as long as proper interaction of the different parts are maintained.

The valve arrangement illustrated in FIG. 9 is an exemplary embodiment of a "push down" design in which the solenoid actuator (45) is positioned above the microfluidic channel (42) in order to push down the membrane portion (46) and close the channel (42), thus closing the valve. In those embodiments, the layer comprising the fluid channels should be sufficiently thin and soft to allow the membrane to deform enough in order to let the valve to fully close. While FIG. 9 shows a channel (42) having a rectangular or square profile, in some instances channels having a rounded profile can be preferred In some embodiments, rounded channels (those made with a rounded instead of square profile, to allow for a better seal. By way of example, rounded channels can be obtained by reflowing patterned photoresist used to make the microfluidic mold or by chemically or physically polishing metal molds. In some embodiments, the shape of the pin surface engaging the membrane to close the valve is also rounded so to match at least a portion of the bottom surface of the channel thus allowing a better closure of the channel In the embodiments exemplified in FIG. 9, the valve arrangement can be operated in combination with a monolithic microfluidic chip. Such arrangement presents a distinct advantage over microfluidic valves that have to be aligned and bonded with a microfluidic chip, because it allows for the use of materials such as SIFEL, PFPE and other compounds which normally cannot be used when two layers need to be aligned and bonded.

In some embodiments, a reinforcing layer or thick layer (44) can be included in the microfluidic assembly (400). The reinforcing layer (44) comprises holes into it to allow the solenoid pin (45) to pass through. The thick layer (44) can be aligned to the top and held in place, either through chemical bonding or by physical means. Although FIG. 9 shows a hole large enough to host both the solenoid (45) and the pin (48), the person skilled in the art will understand that the holes should be only large enough to allow passing through of the small pin (48). In some embodiments, the thick layer (44) will serve to prevent deformations and provide better valve sealing. It will also add stability to the structure, this preventing the microfluidic channel (42) from bursting through the thin membrane (46).

In the assembly herein disclosed, the orientation of the thin membrane (46) within the microfluidic chip does not affect the operation of the valve arrangement within the chip. Therefore, in some embodiments the thin membrane can be located on the upper side of the channel (as shown in FIG. 9), while in other embodiments the membrane can be located on the lower side of the channel (FIG. 10).

In particular, in some embodiments, exemplified by the schematic illustration of FIG. 10, the valve arrangement herein is designed in a "push up" configuration of the pin actuated valve. In particular, in FIG. 10 a solenoid actuator (55) operates by deforming a thin deformable membrane (57) through a pin (58) adjacent the microfluidic channel (52) in a chip or device (51) part of a microfluidic assembly (500).

In the valve arrangement of FIG. 10, the solenoid actuators (55) are positioned on the bottom and the channel (52) is molded into a thick piece of polymer forming the chip (51). Also in those embodiments, the channels (52) can be made with a rounded profile to improve valve sealing possibly to mate with a rounded pin. In the valve arrangement of FIG. 10, the solenoid (55) pushes the pin (58) on the thin membrane (57) along the direction of arrow A2, thus deforming thin membrane (57) and pushing it into the channel (52) to seal it, thus preventing passage of fluid into the channel (52).

In both of the embodiments illustrated in FIGS. 9 and 10, the thin membranes (46) and (57) are part of the channels (42) and (52), respectively and define at least one surface of those channels. In particular, the membranes constitute one wall of the channel, more specifically a deformable wall of the channel. In the embodiment of FIG. 9, walls of the channel (42) are provided both by membrane (46) and by substrate (43). During manufacturing of the microfluidic chip, the substrate or membrane will be placed on top or bottom of the chip upon formation of the various channels and compartments of the chip. In those embodiments, filling the flow channels or any compartment within the chip with a fluid of interest can be advantageously performed before closing the channels (42, 52) and/or another compartment with the substrate (43) or the membrane (57).

In particular, in the embodiments exemplified in FIG. 9, channel (42) is closed by the glass or plastic layer (43), while in embodiments exemplified in FIG. 10 channel (52) is closed by the thin membrane (57).

Accordingly, while in some embodiments, exemplified by FIG. 9, the thin membrane (46) is an integral part of the channel formed in the same material forming the channel, in other embodiments exemplified by FIG. 10, the thin membrane (57) is a separate layer imposed over or below the channel (52). In some embodiments, the layer (43), matrix (41) and thin membrane (46) can be formed in a monolithic piece.

Additionally, in the embodiments, exemplified by the schematic illustration of FIG. 10, the thin membrane (57) can be made of the same material forming the other walls of channel (52) or a different material, thus allowing selection of different materials for different parts of the chip and expanding the material selection choices.

In particular, in some of the embodiments exemplified in FIG. 10 the thin membrane (57) can be manufactured with a deformable material, such as SIFEL or PDMS, which is also a sealant thus allowing an easier closing operation of the channel (52). In some of those embodiments, the flow channels (52) can be manufactured with a chemically robust material, including injection molded material, hard plastic, glass metal and any other material that can be used in a rigid fashion. In other embodiments, the material forming the channel (52) and the material forming the thin membrane (57) are the same.

In embodiments wherein the thin membrane (57) and the channels (52) are formed of a same material (similarly to the embodiments of FIG. 9), the material forming the membrane and the channel must be deformable to the extent that functioning of the thin membrane is allowed, so that in those embodiments the channel cannot be rigid but will have to be deformable, at least to a certain extent.

In some embodiments, the thin membrane (57) of the embodiment of FIG. 10 can be chemically bonded to the chip (51), and/or can be clamped together with said chip and channel by means of a mechanical clamp (56) (schematically shown in FIG. 2) included to improve positioning of the thin membrane and solenoid in the valve arrangement herein described.

In some embodiments, the thin membrane (57) is bonded to the chip (51) by first providing a film of deformable material, and then contacting the film with the chip (51) to cover the channel/compartments formed therein. The film of deformable material is then cured to bond with the chip (51). In these embodiments, the channels and/or compartments of the microfluidic chip are formed after adhesion of the membrane to the microfluidic chip.

In some embodiments, providing a film of deformable material is performed by contacting the deformable material with a flat surface, preferably made of a material with a minimized ability to adhere to the deformable material, and spinning the deformable material on the flat surface to provide the film of the deformable material. In particular, the spinning operation creates a membrane of a certain thickness functional to the spinning speed and the nature of the material used.

Particularly suitable materials for forming the thin membrane (57) are deformable materials, such as SIFEL or PDMS, capable of bonding with a rigid material of choice forming the channel/compartments of the chip (51) such as polypropylene or polystyrene.

Curing of the deformable material can be performed by several methods known in the art including but not limited to UV irradiation, heat, chemical treatment and additional methods identifiable by a skilled person.

In some embodiments, contacting the film of deformable material is performed by placing the chip over the film, to minimize drooling of the deformable material on to the channel.

In some embodiments, contacting the film of deformable material with the chip can be performed on a surface made of a material that has a minimized ability to adhere to the deformable material, e.g. Teflon, when the deformable material is SIFEL.

In some embodiments, the film of deformable material is formed by tensioned sheets and contacting the film of deformable material with the chip can be performed to maintain tension of the tensioned sheet and possibly using an adhesive to seal the film on the chip.

As already noted above, in some embodiments, the chip (51) can further include a mechanical clamp (56) to also hold the thin membrane (57) and the chip (51) in place over a base plate (54) with holes drilled at appropriate places to allow the solenoid (55) to pass through, similarly to what discussed with reference to the embodiment of FIG. 9. In some embodiments, the base plate (54) can also be part of the chip (51) in order to create a sandwich which can be placed on the controlling unit comprising the solenoid actuator (55), as also illustrated in further detail below (see FIGS. 14 and 15).

Figure 11:
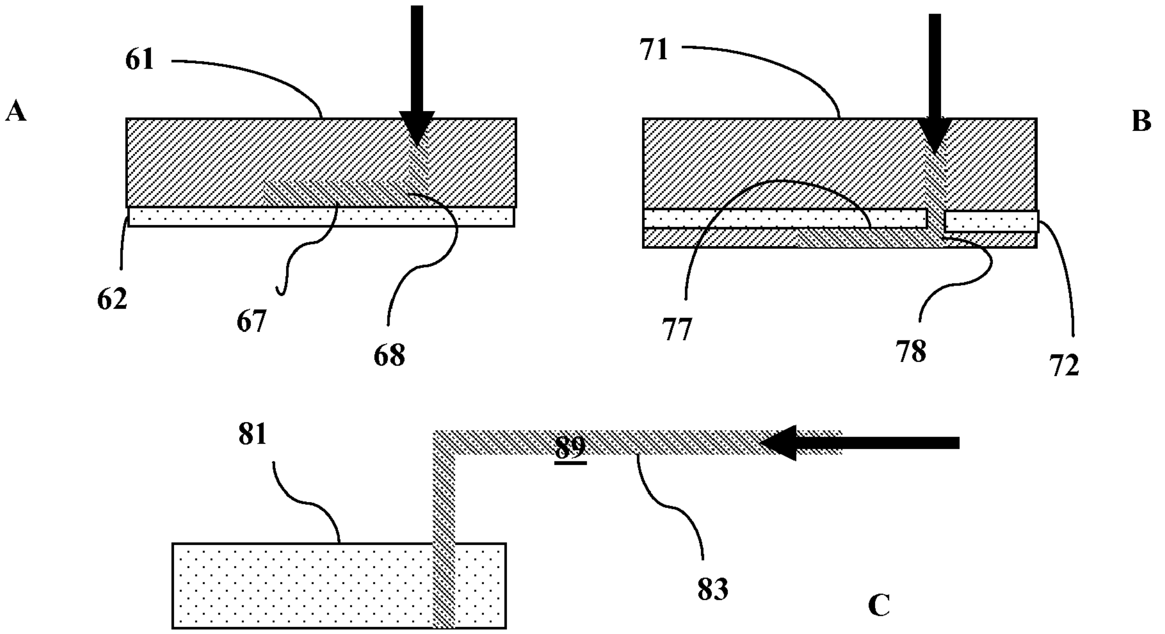
FIG. 11 shows a schematic cross-sectional view of a valve arrangement according to a further embodiment herein disclosed, including an in-chip push-down valve (Panel A), in-chip push up valve (panel B) or an off-chip valve (Panel C), the arrows indicate movement of a pin within the valve arrangement.
Figure 12:
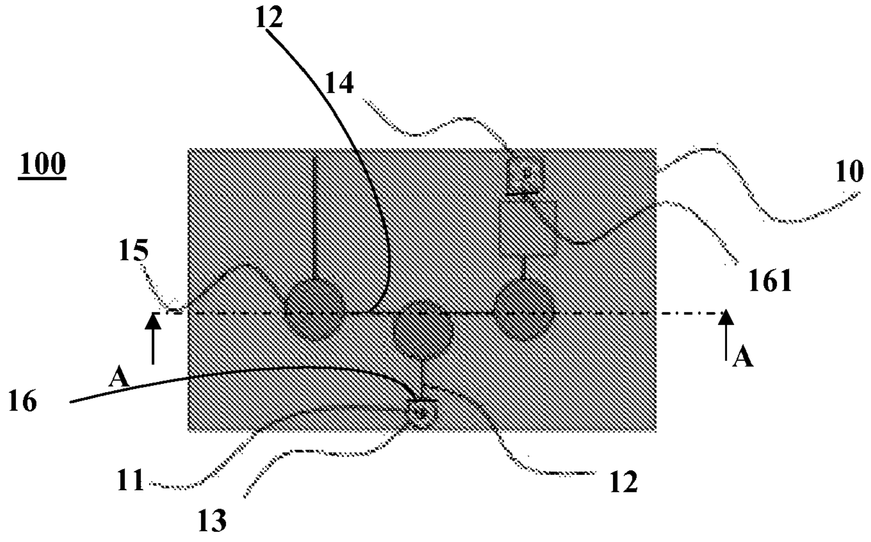
FIG. 12 shows a schematic top view of a valve array on a microfluidic chip according to a still further embodiment herein disclosed.

In some embodiments of the dot matrix valve, the pin mates with a hole in the microfluidic chip (in-chip configuration), or in a hose that has been inserted into the chip (off-chip configuration), as shown in FIG. 11. In those embodiments, the solenoid actuator controls the flow of fluid by pressurizing a control fluid (89), In particular, in some embodiments, exemplified in FIG. 11, the dot matrix type solenoid is included in a hydraulic system wherein a solenoid actuator is operated as a piston moving within a well mated channel in the chip or in a hose and will push on a control fluid such as mineral oil or a gas (68, 78, 89) which includes but is not limited to incompressible fluids and air. In some embodiments, the pressurized oil can be used to push down on a thin membrane (see the push down configuration illustrated in FIG. 1A) or up on a membrane (see the push up configuration illustrated in FIG. 11B), thus actuating a microfluidic valve arrangement such as the one illustrated in FIGS. 9 and 10 respectively.

In those embodiments, two layers can be bonded or held together with a clamp, one layer comprising channels defined as the "control channels" (68) and (78) and the other with channels defined as the "flow channels" (62) and (72). The control fluid (89) will be located in the control channel (68) and (78) and will push on a membrane (67) and (77) separating the control channels (68) and (78) from the flow channels (62) and (72).

In some embodiments, the control fluid (89) is provided to a chip (81) within a hose (83) (see in particular FIG. 11C), so that the hose (83) will be filled with the control fluid (89) which will transmit the force to the chip, either in a push up or push down actuation.

In the embodiments described in the exemplary schematic illustrations of FIGS. 9 and 10, the solenoid exerts pressure on the thin membranes (46) and (57) by acting directly on the thin membrane (46) and (57), and reversibly closes the channel (42) and (52) by pinching the channel. On the other hand, in the embodiments described by the exemplary illustration of FIG. 11, the solenoid acts as a piston inside a control channel (67, 77) formed in the polymer or other material of the chip along a flow channel (62, 72) to control the fluid flow in the flow channels (62, 72). In those embodiments, the control channel is filled with a control fluid, such as gas or mineral oil. In such case, movement of the piston/solenoid inside the control channel creates pressure on the control fluid and through the control fluid to the thin membrane, thus compressing the thin membrane and closing the flow channel.

In some embodiments, movement of the solenoid towards the control channel creates a vacuum in the control channel and therefore a negative pressure on the control fluid and through the control fluid on the thin membrane. In some of those embodiments, such negative pressure is exerted to perform a fluid handling task. For example, a task that requires a small vacuum such as dislocation of a small amount of fluid backward in the fluid channel can be performed, to possibly perform a test or allow a predetermined reaction.

In some embodiments, the thin membrane is located on the upper side of the flow channels to be controlled, and the corresponding valve arrangement is a push-down valve (see FIG. 11A). In some embodiments, the thin membrane is located in the lower side of the flow channels to be controlled, and the corresponding valve arrangement is a push-up valve (see FIG. 11B).

In some embodiments, the valve arrangement is operated in combination with Quake-style valves, such as the ones described in U.S. Pat. Nos. 6,408,878, 6,793,753, 6,899,137, 6,929,030, 7,040,338, 7,144,616, 7,169,314, 7,216,671, all of which are herein incorporated by reference in their entirety.

An exemplary microfluidic chip where the valve arrangement herein described can be operated in combination with a Quake-style valve is the chip described in US Published Patent Application US2006/0263818 to Kartalov et al, also incorporated by reference in its entirety in the present application. Such chip or device will be hereinafter indicated as "Kartalov chip."

The Kartalov chip includes a first layer (see flow layer 32 in FIG. 1 of US2006/0263818) for liquid flows and a second layer wherein another fluid or air could flow (see control layer 36 in FIG. 1 of US2006/0263818). By making the first layer very thin and the second layer very thick, pressurization of the second layer communicates the pressure from the second layer to the first layer to force the first layer into closing the channel. In the Kartalov chip, the pressure is created by a pressurized gas system controlled by micromechanical valves. On the other hand, the present disclosure deals with a pin/membrane combination, that can replace the external source of pressurized gas and the external manifold including valves to control feeding of the gas inside the pressurized gas inside the chip.

In some embodiments of the valve arrangements according to any one of the configurations exemplified by the illustration of FIGS. 9 to 11, the solenoid actuator can be derived from a dot matrix printer which is taken apart and cut so to have individual solenoids to be individually utilized or organized in an arrangement.

In some embodiments, the solenoid actuator and microfluidics can be located on separate components, with the microfluidic component disposable while the solenoid component is a multi-use component, connected and possibly including a controlling unit. In some of those embodiments, the microfluidic portion can be replaced for sterility or other reasons while the solenoid arrangement and the controlling unit is maintained for multiple uses.

In some embodiments, an array of dot matrix style pin operated microfluidic valves can be used to control the flow of fluid in fluid channels and through the channels in the compartments. In particular, in some of those embodiments, a plurality of valves is operated along a channel to create a peristaltic movement of the thin membrane and corresponding fluid flow inside the channel.

In particular, in some embodiments, an array of such valve arrangements can be created, with a controlling unit holding each solenoid pin in place, either on a hinge or some other mounting method. A disposable microfluidic chip is placed in the correct orientation. More in particular, in some embodiments, the array of solenoid pins is lowered into position (or the chip raised) and the chip can be actuated with the solenoid pins.

In some embodiments, the solenoid actuator (45, 55) and the chip (41, 51) are included in separate components of the fluidic circuit (400, 500). More particularly, the solenoid actuator (45, 55) is included in a multiuse controlling unit, while the microfluidic chip (41, 51) is a disposable mono-use microfluidic chip. In particular, in some embodiments, a box or holder can be provided, into which a disposable microfluidic chip can later be placed. The box contains everything needed to carry out the experiment except for the fluidics portion (the microfluidic chip). In this kind of arrangement, the fluidics portion can be disposable.

Reference is made to FIGS. 12 to 15, wherein a solenoid arrangement in combination with a controlling unit and microfluidics are shown. In particular, in FIG. 12, an arrangement (100) is shown including a chip (10) having a schematically shown sample port (11) with a schematically shown capillary tube (13), vent or vacuum port (14) and channels (12) including blood filter (16) and a vapor barrier (161). Also shown is a solenoid array, including solenoid actuator (15). In the cross-sectional view of FIG. 13 (taken along line A-A of FIG. 12), the details of the solenoid-chip interaction are illustrated as shown in inset C of FIG. 13. Inset C shows the pin (18) of the solenoid actuator, the thin membrane (17) and the microchannel (12) in a condition where the valve is open (no contact between pin and membrane). Inset B shows the same arrangement wherein the valve is closed (contact between pin and membrane).

Figure 13:
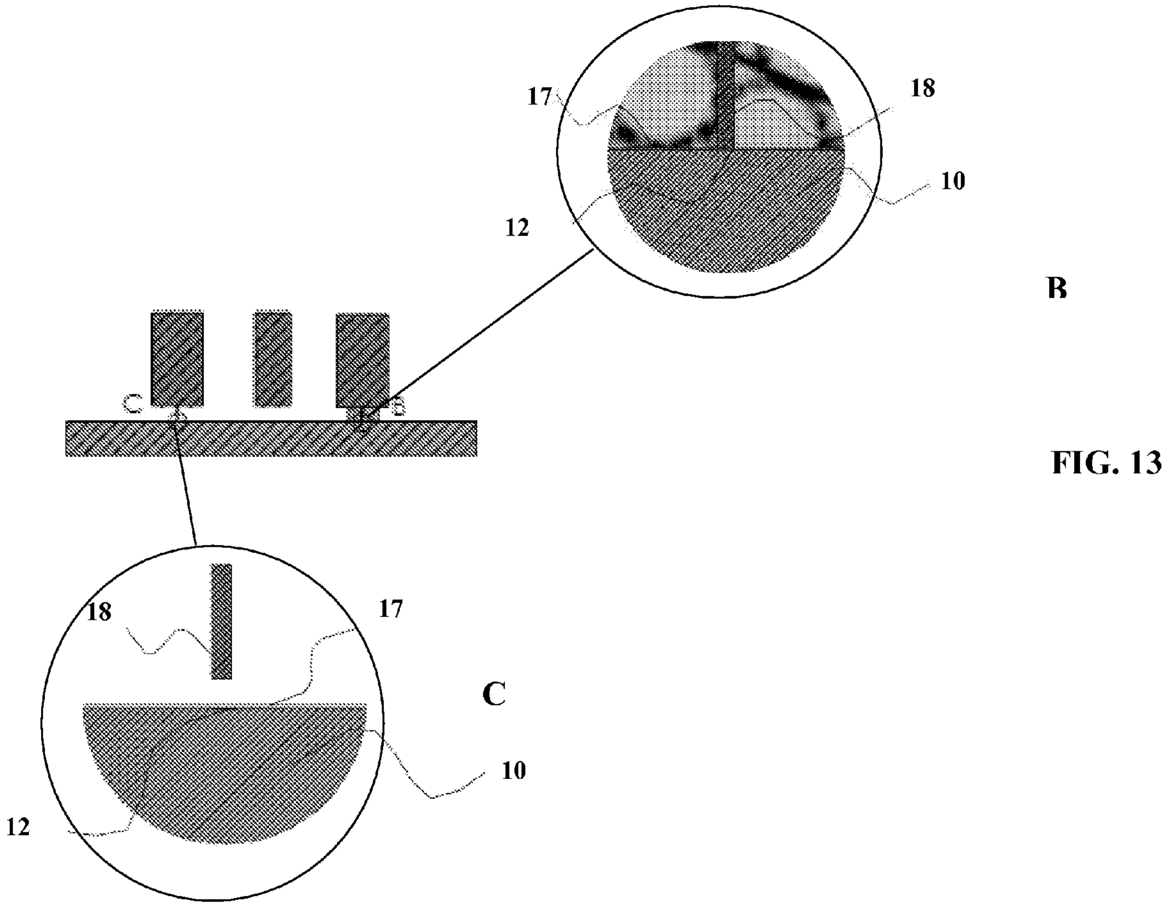
FIG. 13 shows a schematic cross sectional view of the valve array of FIG. 12 along line A-A of FIG. 12.
Figure 14:
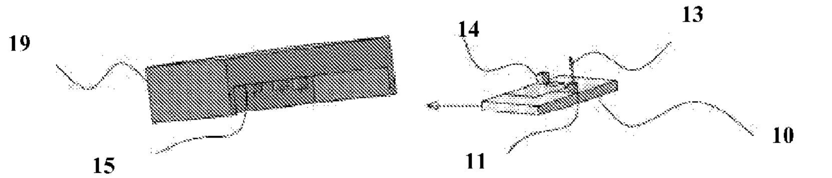
FIG. 14 shows a schematic perspective view of the valve array and microfluidic according to an embodiment herein disclosed.

In the schematic illustration of FIG. 14, the components of the assembly shown in the cross-sectional top view of FIG. 13 are shown before said components are combined together. As shown in the figure, the solenoid actuator (15) is included in a holder (19). Chip (10) is then inserted into holder (19) and aligned, to allow the solenoid arrangement to engage the chip (10) and operate onto it.

In some embodiments, the holder (19) also includes a controlling unit, the controlling unit operating the solenoid valve arrangement. In particular, in some of embodiments, the controlling unit is non-disposable or multiuse unit, while the microfluidics is disposable, i.e. single-use. FIG. 15 shows an embodiment where the solenoid valve array is aligned with the microfluidic chip and where a detecting assembly is also shown.

In both embodiments, the solenoids are usually arranged so to be used in combination with a chip of choice, typically a standard chip, to match predetermined positions on the chip so that when in use the solenoids can operate on those specific positions as desired, e.g. by using an appropriate software. In some embodiments, the solenoid arrangement in the unit is modified after the use but usually a specific arrangement is used multiple times on the same kind of chip, so that one control unit typically corresponds to one type of chip.

In some embodiments, the valve arrangement is the one exemplified in FIG. 11 and each solenoid can operate on one or multiple valves. In some embodiments, wherein the valve arrangement is the one exemplified in FIG. 9 or 10 each solenoid can operate one valve only, with multiple solenoids able to control multiple valves.

In some embodiments, the microfluidic valve or pump can be electrically actuated. In some embodiments of the valve arrangement herein included, the solenoids can be replaced by pins coming down and closing the channels, although in some embodiments a solenoid could be preferred because it can be controlled electrically. Additional arrangements can be operated by other electrical or non electrical means such as pressurized fluid (e.g. air) or a thermostatic operator (e.g. a bimetal coil).

In some embodiments, the valve arrangement or valve arrangement array is actuated by sending an electrical signal to the solenoid, pushing out the pin onto the membrane, causing the channel to pinch off as it pushes against the substrate.

Figure 15:
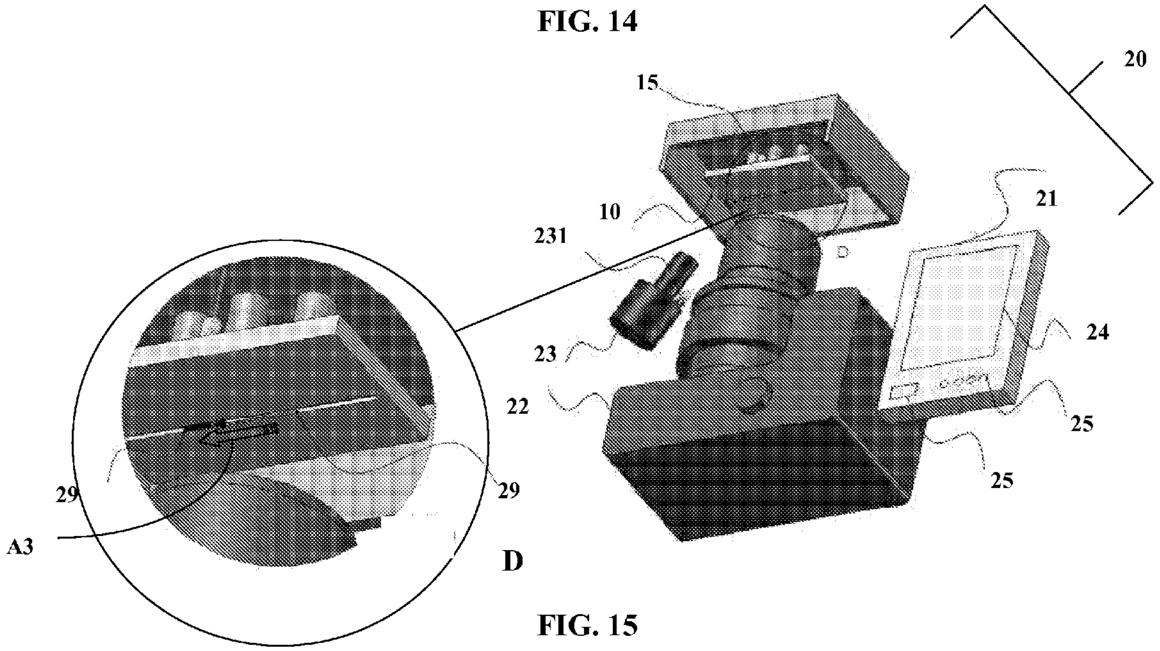
FIG. 15 shows a schematic perspective view of the valve array and microfluidic of FIG. 14 in combination with a light emitter, a detector and a controlling unit according to an embodiment herein disclosed.

In particular, in some embodiments, illustrated in FIG. 15, a controlling unit (20) comprises a reading unit (21) which in the illustration of FIG. 15 is separated from the holder holding the solenoid pins. The reading unit (21) is associated with detectors (22), emitters (23) possibly including a light source (231), electrodes, computing electronics, user displays (24) and controls (25), computer output, sample collection and preparation, internet connectivity etc. The pins can be arranged such that the disposable, sterile chip is placed into a holder, and then a cover or other such device is shut or moved into position and the solenoid pins will be in position to move the fluid in the chip appropriately to perform chemical or biological analysis on a sample. The detectors can be positioned such that the solenoid actuators do not interfere and a proper reading can be taken from the sample in the chip (see in particular FIG. 15, inset D).

In particular, in some embodiments, illustrated in inset D of FIG. 15, a fluid plug (29) in the microchip is detected by the detector (22), that sends an input to the control unit (20), which in turns activates the solenoid actuator (15) to move the fluid plug (29) to a different location on the chip (see arrow A3 in FIG. 15 inset D)

In some embodiments, collection of a sample (e.g. blood urine, saliva, semen, feces, water, food, breastmilk, vaginal secretions, tears, earwax, mucous etc.) is performed and the sample and then processed through appropriate sample preparation steps before introduction into the microfluidic assembly (400) or (500). In the microfluidic assembly, the sample will then be transferred in flow channels by the valve arrangement actuated by the solenoid actuator (pin valves) herein disclosed. In some embodiments, the system includes also a signaling element providing input to a detector in the controlling indicating the location of the sample in the microfluidic assembly.

It is to be understood that the present disclosure is not limited to particular arrangements devices and methods, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. Unless defined otherwise, all technical and scientific terms used herein have the same meaning as commonly understood by one of ordinary skill in the art to which the disclosure pertains. Although any methods and materials similar or equivalent to those described herein can be used in the practice for testing of the disclosure(s), specific examples of appropriate materials and methods are described herein.

The examples set forth above are provided to give those of ordinary skill in the art a complete and description of how to make and use the embodiments of the arrangements, devices, systems and methods herein disclosed, and are not intended to limit the scope of what the applicants regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this application are incorporated by reference to the same extent as if each reference had been incorporated by reference in its entirety individually.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A microfluidic device comprising a storage compartment, the storage compartment adapted to comprise a reagent suitable for a reaction to occur in the microfluidic device, a reaction area, where a reaction involving said reagent is adapted to occur;

a microfluidic channel connecting the storage compartment with the reaction area;

a valve arrangement to control opening and closing of the microfluidic channel; and a membrane adapted to cover at least portion of the storage compartment, reaction area, and microfluidic channel, the membrane being adapted to seal the at least portion of storage compartment, reaction area, and microfluidic channels, upon filling of the storage compartment with the reagent.

2. The microfluidic device of claim 1, wherein the storage compartment includes a first storage compartment and a second storage compartment and the microfluidic channel connects the first storage compartment with the second storage compartment.

3. The microfluidic device of claim 1, wherein storage state of the reagent is compatible with a desired temperature of storage.

4. The microfluidic device of claim 3, wherein said temperature of storage is from 4° C. to room temperature.

5. The microfluidic device of claim 1, wherein the reagents are in a first physical state during a rest state of the microfluidic device and are brought to a second physical state during an operative state of the microfluidic device.

6. The microfluidic device of claim 1, wherein the valve arrangement comprises a solenoid actuator and a membrane, and wherein movement of the solenoid actuator is adapted to deform the membrane thus preventing flow in the microfluidic channels.

7. The microfluidic device of claim 1, further comprising a waste area connected to a vent, wherein, during operation of the microfluidic device, vacuum is adapted to be applied to the vent to control flow in the microfluidic channels in combination with the valve arrangement.

8. The microfluidic device of claim 1, further comprising a microfluidic mixer located along the microfluidic channel.

9. A hermetically sealed bag comprising the microfluidic device of claim 1.

10. A machine reader comprising the microfluidic device of claim 1.

11. The machine reader of claim 10, the machine reader further comprising clamp valves actuated by said machine reader.

12. The microfluidic device of claim 1, further comprising a top cover, the top cover allowing initial storage of liquid and dry substances in the liquid storage compartments and the dry storage compartments.

13. The microfluidic device of claim 1, comprising a top section and a bottom section, the top section being a polymer molded in a layer and the bottom section being a plastic card containing the storage compartments, the reaction area and the microfluidic channels.

14. The microfluidic device of claim 1, the microfluidic device further comprising a clamp to allow connection of the microfluidic device to a substrate.

15. The microfluidic device of claim 14, wherein the clamp is a metal or plastic clamp.

16. The microfluidic device of claim 1, further comprising a cover element including valve clamps, the valve clamps acting as the valve arrangement.

17. The microfluidic device of claim 16, wherein the valve clamps are electromechanically actuated.

18. The microfluidic device of claim 16, wherein the valve clamps are bendable valve clamps.

19. The microfluidic device of claim 1, further comprising a sealing clamp, the sealing clamp adapted to seal the membrane at least over the storage chambers.

20. The microfluidic device of claim 19, wherein the sealing clamp comprises at least one clamp finger, the at least one clamp finger being part of a valve arrangement and adapted to provide a valve control communication between the first storage compartment and the second storage compartment.

21. The microfluidic device of claim 19, wherein the at least one clamp finger and the sealing clamp are independently operable.

22. The microfluidic device of claim 19, further comprising at least one clamp lever to actuate the at least one clamp finger.

23. The microfluidic device of claim 19, wherein the at least one clamp fingers are a plurality of independently operable clamp fingers.

24. The microfluidic device of claim 19, wherein the clamp fingers are adapted to seal other portion of the microfluidic device to prevent the fluid from coming out of the microfluidic device after use.

25. The microfluidic device of claim 1, further including a filter trapped in a microfluidic channel.

26. The microfluidic device of claim 1, wherein the valve arrangement further comprises a deformable membrane, and wherein deformation of the deformable membrane controls opening and closing of the microfluidic channel.

* * * * *